(12) United States Patent
LaBeaume et al.

(10) Patent No.: US 9,551,930 B2
(45) Date of Patent: Jan. 24, 2017

(54) PHOTORESIST COMPOSITION AND ASSOCIATED METHOD OF FORMING AN ELECTRONIC DEVICE

(71) Applicant: Rohm and Haas Electronic Materials LLC, Marlborough, MA (US)

(72) Inventors: Paul J. LaBeaume, Auburn, MA (US); Vipul Jain, North Grafton, MA (US); Suzanne M. Coley, Mansfield, MA (US); James W. Thackeray, Braintree, MA (US); James F. Cameron, Brookline, MA (US); Amy M. Kwok, Shrewsbury, MA (US); David A. Valeri, Leominster, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

(21) Appl. No.: 14/833,278

(22) Filed: Aug. 24, 2015

(65) Prior Publication Data
US 2016/0103391 A1    Apr. 14, 2016

Related U.S. Application Data

(60) Provisional application No. 62/062,348, filed on Oct. 10, 2014.

(51) Int. Cl.
*G03F 7/004*   (2006.01)
*G03F 7/038*   (2006.01)
(Continued)

(52) U.S. Cl.
CPC ............. *G03F 7/038* (2013.01); *C07C 309/12* (2013.01); *C07C 381/12* (2013.01);
(Continued)

(58) Field of Classification Search
CPC ........ G03F 7/0045; G03F 7/0397; G03F 7/20; G03F 7/30; G03F 7/38; C07C 381/12; C07C 309/12; C08F 220/38; C08F 220/24; C08F 220/18; C08F 220/28; H01L 21/0274; H01L 21/0275
(Continued)

(56) References Cited

U.S. PATENT DOCUMENTS 5,130,392 A    7/1992 Schwalm et al.
5,945,250 A    8/1999 Aoai et al.
(Continued)

FOREIGN PATENT DOCUMENTS

JP    2013095880 A    5/2013

OTHER PUBLICATIONS

Liu et al., "Novel Polymeric Sulfonium Photacid Generator and Its Application for Chemically Amplified Photoresists" Proc. of SPIE vol. 9051 (2014) 905124-1-905124-8.
(Continued)

*Primary Examiner* — Amanda C Walke
(74) *Attorney, Agent, or Firm* — Cantor Colburn LLP

(57) ABSTRACT

A photoresist composition includes a first polymer in which at least half of the repeat units are photoacid-generating repeat units, and a second polymer that exhibits a change in solubility in an alkali developer under the action of acid. In the first polymer, each of the photoacid-generating repeat units comprises photoacid-generating functionality and base-solubility-enhancing functionality.

6 Claims, 4 Drawing Sheets

(51) Int. Cl.
  *C07C 309/12* (2006.01)
  *C07C 381/12* (2006.01)
  *C08F 220/18* (2006.01)
  *C08F 220/24* (2006.01)
  *C08F 220/28* (2006.01)
  *C08F 220/38* (2006.01)
  *G03F 7/039* (2006.01)
  *G03F 7/16* (2006.01)
  *G03F 7/20* (2006.01)
  *G03F 7/32* (2006.01)
  *G03F 7/38* (2006.01)
  *H01L 21/027* (2006.01)

(52) U.S. Cl.
  CPC .......... *C08F 220/18* (2013.01); *C08F 220/24* (2013.01); *C08F 220/28* (2013.01); *C08F 220/38* (2013.01); *G03F 7/0045* (2013.01); *G03F 7/0397* (2013.01); *G03F 7/16* (2013.01); *G03F 7/20* (2013.01); *G03F 7/32* (2013.01); *G03F 7/38* (2013.01); *H01L 21/0274* (2013.01)

(58) Field of Classification Search
  USPC .... 430/311, 270.1, 322, 325, 329, 330, 913; 526/243, 268, 245, 280
  See application file for complete search history.

(56) References Cited

U.S. PATENT DOCUMENTS

| | | | |
|---|---|---|---|
| 8,927,191 B2 | 1/2015 | Tsuchiya et al. | |
| 8,945,814 B2 | 2/2015 | Cameron et al. | |
| 8,987,386 B2 | 3/2015 | Utsumi et al. | |
| 2008/0102407 A1* | 5/2008 | Ohsawa | C08F 20/22 430/286.1 |
| 2009/0233223 A1* | 9/2009 | Tachibana | G03F 7/0045 430/270.1 |
| 2009/0269696 A1* | 10/2009 | Ohsawa | C08F 220/18 430/270.1 |
| 2010/0055608 A1* | 3/2010 | Ohashi | C07D 493/18 430/270.1 |
| 2010/0099042 A1 | 4/2010 | Ohashi et al. | |
| 2011/0159429 A1 | 6/2011 | Thackeray et al. | |
| 2011/0177453 A1 | 7/2011 | Masubuchi et al. | |
| 2012/0129103 A1* | 5/2012 | Ohsawa | C07C 309/12 430/285.1 |
| 2012/0282551 A1 | 11/2012 | Matsuzawa et al. | |
| 2012/0322006 A1 | 12/2012 | Kato et al. | |
| 2013/0065182 A1 | 3/2013 | Mori et al. | |
| 2013/0209937 A1 | 8/2013 | Takihana et al. | |
| 2013/0252180 A1 | 9/2013 | Dazai et al. | |
| 2013/0337378 A1* | 12/2013 | Ohashi | G03F 7/027 430/270.1 |
| 2014/0080060 A1 | 3/2014 | Labeaume | |
| 2014/0080062 A1 | 3/2014 | Thackeray et al. | |
| 2014/0186769 A1 | 7/2014 | Kaiho et al. | |
| 2014/0186770 A1 | 7/2014 | Aqad et al. | |
| 2015/0093708 A1 | 4/2015 | Labeaume | |
| 2015/0177615 A1 | 6/2015 | Jain et al. | |
| 2016/0002199 A1 | 1/2016 | Cameron et al. | |
| 2016/0070169 A1 | 3/2016 | Bozano et al. | |
| 2016/0102157 A1 | 4/2016 | Jain et al. | |
| 2016/0102158 A1 | 4/2016 | Labeaume et al. | |
| 2016/0103391 A1 | 4/2016 | Labeaume et al. | |
| 2016/0103392 A1 | 4/2016 | Labeaume et al. | |

OTHER PUBLICATIONS

Nakamura et al., "Photoresist Film Analysis to Investigate LWR Generation Mechanism" Proc. of SPIE vol. 8682 (2013) 86821H-1-86821H-13.

Oh et al., "The Noble Resists Composed of Cationic and Anionic Polymerizable PAGS" Proc. of SPIE vol. 7140 (2008) 714031-1-714031-9.

Satyanarayana et al., "Design and Synthesis of Novel Resist Materials for EUVL" Proc. of SPIE vol. 9049 (2014) 90481W-1-90481W-7.

Non-Final Office Action dated Feb. 25, 2016; U.S. Appl. No. 14/833,284, filed Aug. 24, 2015 (15 pages).

Non-Final Office Action dated Feb. 26, 2016; U.S. Appl. No. 14/833,284, filed Aug. 24, 2015 (15 pages).

Non-Final Office Action dated Jul. 28, 2016; U.S. Appl. No. 14/833,273, filed Aug. 24, 2015 (21 pages).

* cited by examiner

PHOTORESIST COMPOSITION AND ASSOCIATED METHOD OF FORMING AN ELECTRONIC DEVICE

FIELD

The present invention relates to a photoresist composition comprising a photoacid-generating polymer.

INTRODUCTION

As feature sizes of integrated circuits continue to shrink, next generation lithographic processes struggle to fit the stringent requirements to extend Moore's Law. It has long been recognized that increased photoacid generator (PAG) non-uniformity and acid diffusion have limited photoresist resolution, worsened line width roughness (LWR) (see, e.g., Nakamura et. al., Proc. SPIE 2013, 8682, 86821H-1), limited exposure latitude, and generally degraded photolithographic performance for chemically amplified resists. In the past, polymer-bound-PAG (PBP) systems have been implemented to increase PAG uniformity and control acid diffusion (see, e.g., Oh et. al., Proc. SPIE 2008, 7140 714031, pages 1-9; and U.S. Pat. No. 5,945,250 B2 to Aoai et al.). More recently, increased concentration of PAG in the matrix has been shown to further enhance lithographic performance, particularly when combined with a PBP system (U.S. Patent Application Publication No. US 2014/0080062 A1 of Thackeray et al.). Despite these advances, there remains a need for photoresist compositions providing one or more of decreased critical dimension uniformity, increased contact hole exposure latitude, increased line-space exposure latitude, and decreased line width roughness.

SUMMARY

One embodiment is a photoresist composition comprising: a first polymer comprising 50 to 100 mole percent of photoacid-generating repeat units, wherein each of the photoacid-generating repeat units comprises (a) photoacid-generating functionality and (b) base-solubility-enhancing functionality selected from the group consisting of tertiary carboxylic acid esters, secondary carboxylic acid esters wherein the secondary carbon is substituted with at least one unsubstituted or substituted $C_{6-40}$ aryl, acetals, ketals, lactones, sultones, alpha-fluorinated esters, beta-fluorinated esters, alpha,beta-fluorinated esters, polyalkyleneglycols, alpha-fluorinated alcohols, and combinations thereof; and a second polymer that exhibits a change in solubility in an alkali developer under the action of acid.

Another embodiment is a method of forming an electronic device, comprising: (a) applying a layer of the photoresist composition on a substrate; (b) pattern-wise exposing the photoresist composition layer to activating radiation; and (c) developing the exposed photoresist composition layer to provide a resist relief image.

These and other embodiments are described in detail below.

DETAILED DESCRIPTION

Figure 1:
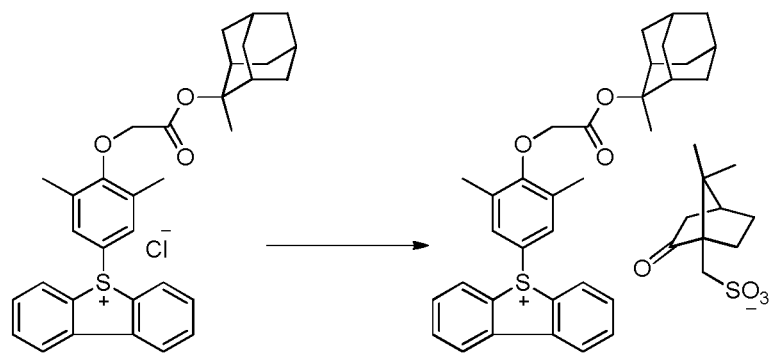
FIG. 1 is a synthetic scheme for the preparation of 5-(3,5-dimethyl-4-(2-(((1R,3S,5r,7r)-2-methyladamantan-2-yl)oxy)-2-oxoethoxy)phenyl)-5H-dibenzo[b,d]thiophen-5-ium ((1S,4S)-7,7-dimethyl-2-oxobicyclo[2.2.1]heptan-1-yl)methanesulfonate.

The present inventors have determined that the photolithographic performance of a photoresist composition can be improved by the incorporation of a first polymer in which at least 50 mole percent of the repeat units are photoacid-generating repeat units, and a second polymer that exhibits a change in solubility in an alkali developer under the action of acid. In the first polymer, each of the photoacid-generating repeat units comprises photoacid-generating functionality and base-solubility-enhancing functionality. The improvement in photolithographic performance can be manifested as one or more of decreased critical dimension uniformity, decreased dose to clear energy, and increased contrast slope.

Thus, one embodiment is a photoresist composition comprising: a first polymer comprising 50 to 100 mole percent of photoacid-generating repeat units, wherein each of the photoacid-generating repeat units comprises (a) photoacid-generating functionality and (b) base-solubility-enhancing functionality selected from the group consisting of tertiary carboxylic acid esters, secondary carboxylic acid esters wherein the secondary carbon is substituted with at least one unsubstituted or substituted $C_{6-40}$ aryl, acetals, ketals, lactones, sultones, alpha-fluorinated esters, beta-fluorinated esters, alpha,beta-fluorinated esters, polyalkyleneglycols, alpha-fluorinated alcohols, and combinations thereof; and a second polymer that exhibits a change in solubility in an alkali developer under the action of acid.

In some embodiments, the first polymer comprises, based on 100 mole percent of total repeat units, 60 to 100 mole percent of photoacid-generating repeat units, specifically 70 to 100 mole percent of photoacid-generating repeat units, more specifically 80 to 100 mole percent of photoacid-generating repeat units, still more specifically 90 to 100 mole percent of photoacid-generating repeat units, even more specifically 95 to 100 mole percent of photoacid-generating repeat units. As used herein, the term "repeat unit" refers to divalent unit that is the residue of a polymerizable monomer. Conversely, "repeat unit" does not include monovalent groups, such as a terminal group derived from a polymerization initiator.

The photoacid-generating repeat units of the first polymer include photoacid-generating functionality. The photoacid-generating functionality can be chemically neutral, in the sense that it does not include an anion or a cation. Examples of chemically neutral photoacid-generating functionality include

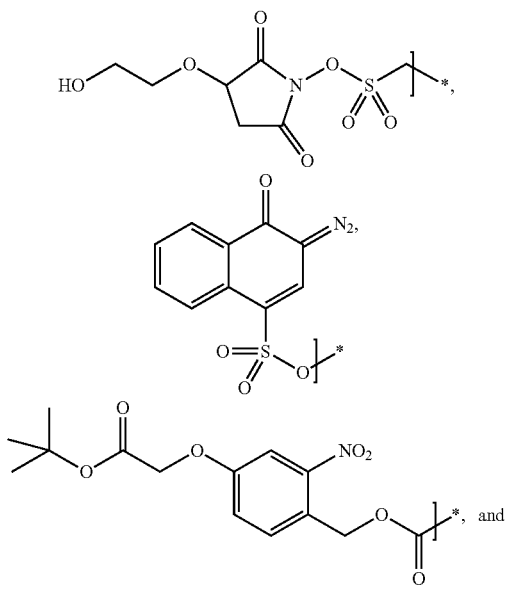

-continued

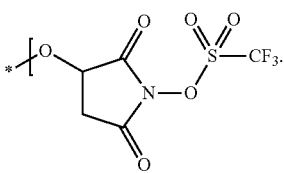

Although the examples shown above are monovalent, the photoacid-generating functionality can also be divalent, trivalent, or tetravalent, depending on the structure of the photoacid-generating repeat unit.

Alternatively, the photoacid-generating functionality of the first polymer can comprise a cation and an anion. For example, the cation can comprise a dihydrocarbyliodonium group or a trihydrocarbylsulfonium group, For example, the anion can comprise sulfonate ($-SO_3^-$), sulfonamidate (anion of sulfonamide; $-S(O)_2N^-R^3$, wherein $R^3$ is H or unsubstituted or substituted $C_{1-12}$ hydrocarbyl), or sulfonimidate (anion of sulfonimide; $-S(O)_2N^-S(O)_2R^3$, wherein $R^3$ is H or unsubstituted or substituted $C_{1-12}$ hydrocarbyl). As used herein, the term "hydrocarbyl", whether used by itself, or as a prefix, suffix, or fragment of another term, refers to a residue that contains only carbon and hydrogen unless it is specifically identified as "substituted hydrocarbyl". The hydrocarbyl residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. When the hydrocarbyl residue is described as substituted, it can contain heteroatoms in addition to carbon and hydrogen.

In addition to photoacid-generating functionality, each photoacid-generating repeat unit of the first polymer comprises base-solubility-enhancing functionality. Base-solubility-enhancing functionality includes functional groups that are base-soluble (e.g., polyalkyleneglycols, alpha-fluorinated alcohols); functional groups that are base-soluble after acid-catalyzed deprotection (e.g., tertiary esters, acetals, ketals, secondary carboxylic acid esters wherein the secondary carbon is substituted with at least one unsubstituted or substituted $C_{6-40}$ aryl); and functional groups that are base-soluble after base-catalyzed deprotection (e.g., fluorinated esters, lactones, sultones). Examples of base-solubility-enhancing functionality include tertiary carboxylic acid esters, secondary carboxylic acid esters wherein the secondary carbon is substituted with at least one unsubstituted or substituted $C_{6-40}$ aryl, acetals, ketals, lactones, sultones, alpha-fluorinated esters, beta-fluorinated esters, alpha,beta-fluorinated esters, polyalkyleneglycols, alpha-fluorinated alcohols, and combinations thereof. In some embodiments, the base-solubility-enhancing functionality is a tertiary carboxylic acid ester, an acetal, a ketal, a lactone, or a combination thereof. In some embodiments, the base-solubility-enhancing functionality is a tertiary carboxylic acid ester, a lactone, or a combination thereof. In some embodiments, the base-solubility-enhancing functionality resides in a photoacid-generating cation.

In some embodiments, the photoacid-generating repeat unit comprises a polymer-bound anion and a non-polymer-bound cation. For example, the photoacid-generating repeat units can have the structure

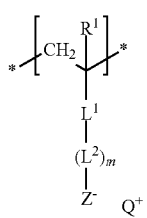

wherein $R^1$ is independently in each of the repeat units H, F, —CN, $C_{1-10}$ alkyl, or $C_{1-10}$ fluoroalkyl; $L^1$ is independently in each of the repeat units —O—, —C(O)—O—, unsubstituted $C_{6-18}$ arylene, or substituted $C_{6-18}$ arylene; m is independently in each of the repeat units 0 or 1; $L^2$ is independently in each of the repeat units an unsubstituted or substituted $C_{1-20}$ hydrocarbylene, wherein the substituted $C_{1-20}$ hydrocarbylene can, optionally, include one or more in-chain divalent heteroatom-containing groups such as —O—, —S—, —$NR^2$, —$PR^2$—, —C(O)—, —OC(O)—, —C(O)O—, —OC(O)O—, —N($R^2$)C(O)—, —C(O)N($R^2$)—, —OC(O)N($R^2$)—, —N($R^2$)C(O)O—, —S(O)—, —S(O)$_2$—, —N($R^2$)S(O)$_2$—, —S(O)$_2$N($R^2$)—, —OS(O)$_2$—, or —S(O)$_2$O—, wherein $R^2$ is H or $C_{1-12}$ hydrocarbyl; $Z^-$ is independently in each of the repeat units sulfonate (—SO$_3^-$), sulfonamidate (anion of sulfonamide; —S(O)$_2$N$^-R^3$, wherein $R^3$ is H or unsubstituted or substituted $C_{1-12}$ hydrocarbyl), or sulfonimidate (anion of sulfonimide; —S(O)$_2$N$^-$S(O)$_2R^3$, wherein $R^3$ is H or unsubstituted or substituted $C_{1-12}$ hydrocarbyl); and $Q^+$ is photoacid-generating cation; wherein at least one of $L^1$, $L^2$ (when m is 1), and $Q^+$ comprises the base-solubility-enhancing functionality. In other words, if m is zero, then at least one of $L^1$ and $Q^+$ comprises base-solubility-enhancing functionality, and if m is one, then at least one of $L^1$, $L^2$, and $Q^+$ comprises base-solubility-enhancing functionality.

In specific embodiments of the photoacid-generating repeat unit comprising a polymer-bound anion and a non-polymer-bound cation, $R^1$ is independently in each of the repeat units H or methyl; $L^1$ is —C(O)—O— in each of the repeat units; m is 1 in each of the repeat units; $L^2$ is independently in each of the repeat units a fluorine-substituted $C_{2-20}$ hydrocarbylene, wherein the fluorine-substituted $C_{2-20}$ hydrocarbylene can, optionally, include one or more in-chain divalent heteroatom-containing groups that is —O—, —OC(O)—, or —C(O)O—; Z is sulfonate (—SO$_3^-$) in each of the repeat units; and $Q^+$ is independently in each of the repeat units an unsubstituted or substituted tri($C_{1-60}$-hydrocarbyl)sulfonium ion, or an unsubstituted or substituted di($C_{1-60}$-hydrocarbyl)iodonium ion. When $R^1$ is H and $L^1$ is —C(O)—O—, then the repeat unit is an acrylate ester. When $R^1$ is methyl and $L^1$ is —C(O)—O—, then the repeat unit is a methacrylate ester.

In some embodiments, the photoacid-generating functionality comprises a polymer-bound cation and a non-polymer-bound anion. For example the photoacid-generating repeat units have the structure

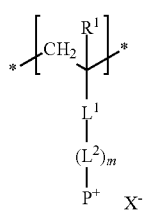

wherein $R^1$ is independently in each of the repeat units H, F, —CN, $C_{1-10}$ alkyl, or $C_{1-10}$ fluoroalkyl; $L^1$ is independently in each of the repeat units —O—, —C(O)—O—, unsubstituted $C_{6-18}$ arylene, or substituted $C_{6-18}$ arylene; m is independently in each of the repeat units 0 or 1; $L^2$ is independently in each of the repeat units an unsubstituted or substituted $C_{1-20}$ hydrocarbylene, wherein the substituted $C_{1-20}$ hydrocarbylene can, optionally, include one or more in-chain divalent heteroatom-containing groups that is —O—, —S—, —$NR^2$, —$PR^2$—, —C(O)—, —OC(O)—, —C(O)O—, —OC(O)O—, —N($R^2$)C(O)—, —C(O)N($R^2$)—, —OC(O)N($R^2$)—, —N($R^2$)C(O)O—, —S(O)—, —S(O)$_2$—, —N($R^2$)S(O)$_2$—, —S(O)$_2$N($R^2$)—, —OS(O)$_2$—, or —S(O)$_2$O—, wherein $R^2$ is H or $C_{1-12}$ hydrocarbyl; $P^+$ is independently in each of the repeat units a monovalent group comprising an unsubstituted or substituted tri($C_{1-60}$-hydrocarbyl)sulfonium ion, or an unsubstituted or substituted di($C_{1-60}$-hydrocarbyl)iodonium ion; and $X^-$ is a monovalent anion; wherein at least one of $L^1$, $L^2$ (when m is 1), and $Q^+$ comprises the base-solubility-enhancing functionality.

In specific embodiments of the photoacid-generating repeat unit comprising a polymer-bound cation and a non-polymer-bound anion, $R^1$ is independently in each of the repeat units H or methyl; $L^1$ is —C(O)—O— in each of the repeat units; $P^+$ is independently in each of the repeat units a monovalent group comprising an unsubstituted or substituted tri($C_{1-60}$-hydrocarbyl)sulfonium ion; and $X^-$ comprises sulfonate (—SO$_3^-$) in each of the repeat units. When $R^1$ is H and $L^1$ is —C(O)—O—, then the repeat unit is an acrylate ester. When $R^1$ is methyl and $L^1$ is —C(O)—O—, then the repeat unit is a methacrylate ester.

In some embodiments of the first polymer, the photoacid-generating repeat units of the first polymer are derived from a single monomer. Alternatively, the photoacid-generating repeat units of the first polymer can be derived from at least two different monomers.

The first polymer comprises 50 to 100 mole percent of photoacid-generating repeat units, based on 100 mole percent of total repeat units. When the first polymer comprises less than 100 mole percent of photoacid generating repeat units, the other repeat units can comprise photoacid-generating functionality or not, and they can comprise base-solubility-enhancing functionality or not. Examples of monomers from which such other repeat units can be derived are

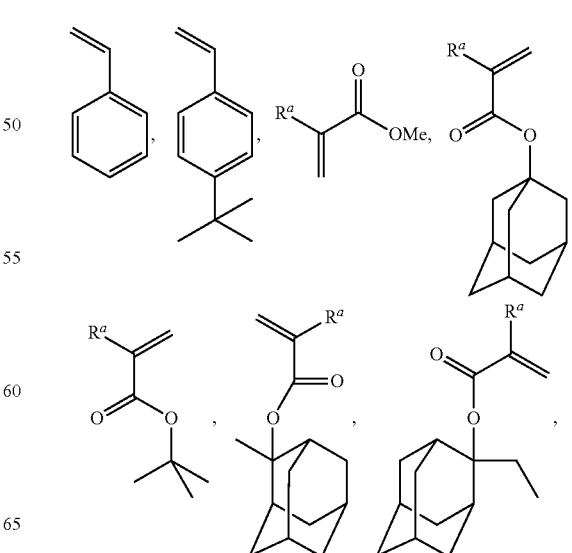

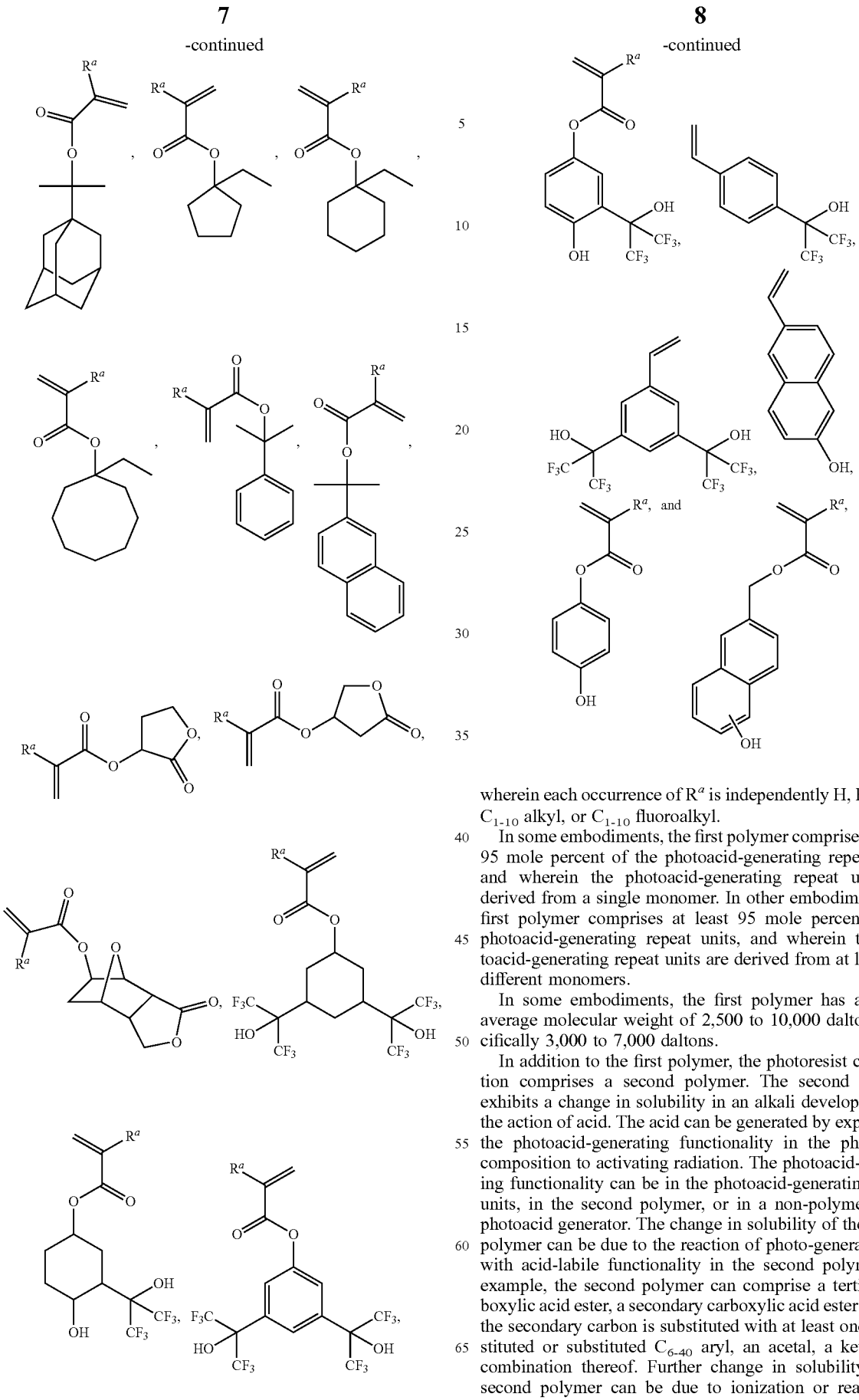

wherein each occurrence of $R^a$ is independently H, F, —CN, $C_{1-10}$ alkyl, or $C_{1-10}$ fluoroalkyl.

In some embodiments, the first polymer comprises at least 95 mole percent of the photoacid-generating repeat units, and wherein the photoacid-generating repeat units are derived from a single monomer. In other embodiments, the first polymer comprises at least 95 mole percent of the photoacid-generating repeat units, and wherein the photoacid-generating repeat units are derived from at least two different monomers.

In some embodiments, the first polymer has a weight average molecular weight of 2,500 to 10,000 daltons, specifically 3,000 to 7,000 daltons.

In addition to the first polymer, the photoresist composition comprises a second polymer. The second polymer exhibits a change in solubility in an alkali developer under the action of acid. The acid can be generated by exposure of the photoacid-generating functionality in the photoresist composition to activating radiation. The photoacid-generating functionality can be in the photoacid-generating repeat units, in the second polymer, or in a non-polymer-bound photoacid generator. The change in solubility of the second polymer can be due to the reaction of photo-generated acid with acid-labile functionality in the second polymer. For example, the second polymer can comprise a tertiary carboxylic acid ester, a secondary carboxylic acid ester wherein the secondary carbon is substituted with at least one unsubstituted or substituted $C_{6-40}$ aryl, an acetal, a ketal, or a combination thereof. Further change in solubility of the second polymer can be due to ionization or reaction of second polymer functional groups with the base in the alkali developer. For example, a tertiary carboxylic acid ester in the second polymer can react with acid to form a carboxylic acid and a tertiary alcohol, and the carboxylic acid can react with base to form a carboxylate anion.

In very specific embodiments, the second polymer comprises 1 to 70 mole percent of acid-labile repeat units, 0 to 60 mole percent of base-labile repeat units, 0 to 60 mole percent of base-soluble repeat units, and 0 to 50 mole percent of photoacid-generating repeat units, wherein the sum of acid-labile repeat units, base-labile repeat units, base-soluble repeat units, and photoacid-generating repeat units in the second polymer is 100 mole percent.

In addition to the first polymer and the second polymer, photoresist composition optionally further includes a photo-destroyable quencher, an amine or amide additive to adjust photospeed and/or acid diffusion, a solvent, a surfactant, or a combination thereof.

The photoresist composition can include an amine or amide compound. These compounds are sometimes referred to as "quenchers" but are chemically distinct from the photo-destroyable quencher. The amine or amide compounds include $C_{1-30}$ organic amines, imines, or amides, or can be a $C_{1-30}$ quaternary ammonium salt of a strong base (e.g., a hydroxide or alkoxide) or a weak base (e.g., a carboxylate). Exemplary amine or amide compounds include amines such as Troger's base, hindered amines such as diazabicycloundecene (DBU) and diazabicyclononene (DBN), N-protected amines such as N-t-butylcarbonyl-1,1-bis(hydroxymethyl)-2-hydroxyethylamine, and ionic compounds including quaternary alkyl ammonium salts such as tetrabutylammonium hydroxide (TBAH) and tetrabutyl ammonium lactate.

Examples of photo-destroyable quenchers include triphenylsulfonium hydroxide, triphenylsulfonium 3-hydroxyadamantane carboxylate, triphenylsulfonium camphorsulfonate, and t-butylphenyldibenzothiophenium 1-adamantanecarboxylate.

Solvents generally suitable for dissolving, dispensing, and coating the components include anisole; esters including ethyl lactate, methyl 2-hydroxybutyrate (HBM), n-butyl acetate, 1-methoxy-2-propyl acetate (also referred to as propylene glycol methyl ether acetate, PGMEA), methoxyethyl propionate, ethoxyethyl propionate, and gamma-butyrolactone; alcohols including 1-methoxy-2-propanol (also referred to as propylene glycol methyl ether, PGME), and 1-ethoxy-2 propanol; ketones including cyclohexanone and 2-heptanone; and combinations thereof.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

In a very specific embodiment of the photoresist composition, the second polymer comprises 10 to 65 mole percent of acid-labile repeat units, 0 to 50 weight percent of base-labile repeat units, 0 to 40 mole percent of base-soluble repeat units, and 1 to 15 mole percent, specifically 2 to 10 mole percent, of photoacid-generating repeat units; the photoacid-generating repeat units of the first polymer have the structure

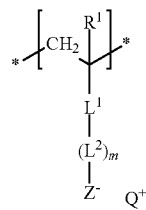

wherein $R^1$ is independently in each of the photoacid-generating repeat units H or methyl; $L^1$ is —C(O)—O— in each of the photoacid-generating repeat units; m is 1 in each of the photoacid-generating repeat units; $L^2$ is independently in each of the photoacid-generating repeat units a fluorine-substituted $C_{2-20}$ hydrocarbylene, wherein the fluorine-substituted $C_{2-20}$ hydrocarbylene can, optionally, include one or more in-chain divalent heteroatom-containing groups that is —O—, —OC(O)—, or —C(O)O—; $Z^-$ is sulfonate ($—SO_3^-$) in each of the repeat units; and $Q^+$ is independently in each of the photoacid-generating repeat units an unsubstituted or substituted tri($C_{1-40}$-hydrocarbyl)sulfonium ion, or an unsubstituted or substituted di($C_{1-40}$-hydrocarbyl) iodonium ion; and at least one of $L^1$, $L^2$ (when m is 1), and $Q^+$ comprises the base-solubility-enhancing functionality; and the photoresist composition comprises, on a dry weight basis, 20 to 80 weight percent of the first polymer, 10 to 60 weight percent of the second polymer, and 0.5 to 10 weight percent of a quencher.

The photoresist composition can be used to form a film comprising the photoresist, where the film on the substrate constitutes a coated substrate. Such a coated substrate includes: (a) a substrate having one or more layers to be patterned on a surface thereof; and (b) a layer of the photoresist composition over the one or more layers to be patterned. Preferably, patterning is carried out using ultraviolet radiation at wavelength of less than 248 nm, and in particular, at 193 nm or 13.4 nm. A method of forming an electronic device includes: (a) applying a layer of the photoresist composition on a substrate; (b) pattern-wise exposing the photoresist composition layer to activating radiation; and (c) developing the exposed photoresist composition layer to provide a resist relief image. In some embodiments, the radiation is ultraviolet (UV), extreme ultraviolet (EUV) or electron beam (e-beam) radiation.

Developing the pattern can be accomplished by either positive tone development (PTD) in which the pattern-wise exposed region is removed by the action of an aqueous base developer such as aqueous tetramethylammonium hydroxide (TMAH). An exemplary positive tone developer is 0.26 Normal aqueous TMAH. Alternatively, the same pattern-wise exposure can be developed using an organic solvent developer to provide a negative tone development (NTD) in which the unexposed region of a pattern is removed by the action of a negative tone developer. Useful solvents for negative tone development include those also useful for dissolving, dispensing, and coating. Exemplary negative tone developer solvents include propylene glycol methyl ether acetate (PGMEA), methyl 2-hydroxyisobutyrate (HBM), n-butyl acetate, methoxyethyl propionate, ethoxyethyl propionate, and gamma-butyrolactone, cyclohexanone, 2-heptanone, and combinations thereof. A method of making a pattern thus includes pattern-wise exposing a photoresist composition layer with actinic radiation, and developing the pattern by treatment with an aqueous alkaline developer to form a positive tone relief image, or with an organic solvent developer to form a negative tone relief image.

Substrates can be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. The surfaces of substrates herein can include critical dimension layers to be patterned including, for example, one or more gate-level layers or other critical dimension layer on the substrates for semiconductor manufacture. The substrates can be formed as circular wafers having dimensions such as, for example, 200 millimeters, 300 millimeters, or larger in diameter, or other dimensions useful for wafer fabrication.

The invention is further illustrated by the following non-limiting examples.

Example 1

FIG. 1 is a synthetic scheme for the preparation of 5-(3,5-dimethyl-4-(2-(((1R,3S,5r,7r)-2-methyladamantan-2-yl)oxy)-2-oxoethoxy)phenyl)-5H-dibenzo[b,d]thiophen-5-ium ((1S,4S)-7,7-dimethyl-2-oxobicyclo[2.2.1]heptan-1-yl)methanesulfonate.

5-(3,5-Dimethyl-4-(2-(((1R,3S,5r,7r)-2-methyladamantan-2-yl)oxy)-2-oxoethoxy)phenyl)-5H-dibenzo[b,d]thiophen-5-ium ((1S,4S)-7,7-dimethyl-2-oxobicyclo[2.2.1]heptan-1-yl)methanesulfonate 5-(3,5-dimethyl-4-(2-(((1R,3S,5r,7r)-2-methyladamantan-2-yl)oxy)-2-oxoethoxy)phenyl)-5H-dibenzo[b,d]thiophen-5-ium ((1S,4S)-7,7-dimethyl-2-oxobicyclo[2.2.1]heptan-1-yl)methanesulfonate chloride (19.4 g, 35.6 mmol) and sodium camphorsulfonate (9.52 g, 37.4 mmol) were dissolved in dichloromethane (200 mL) and water (200 mL) and stirred at room temperature overnight. The layers were separated and the organic phase washed with water (6×150 mL) and concentrated. The crude solid was dissolved in minimal dichloromethane, precipitated into methyl tert-butyl ether (500 mL), filtered and dried to afford the title compound (19.0 g, 72%) as a white solid. $^1$H NMR (500 MHz, (CD$_3$)$_2$CO) δ: 8.52 (d, J=7.8 Hz, 2H), 8.33 (d, J=7.8 Hz, 2H), 7.97 (dt, J=8.4, 0.9 Hz, 2H), 7.76 (dt, J=8.1, 0.9 Hz, 2H), 7.32 (s, 2H), 4.56 (s, 2H), 2.86 (d, J=17.7 Hz, 1H), 2.72 (t, J=7.5 Hz, 1H), 2.35 (d, J=17.7 Hz, 1H), 2.22 (s, 6H), 2.13-2.28 (m, 2H), 1.44-1.97 (m, 26H), 1.26 (d, J=9 Hz, 1H).

Example 2

Figure 2:
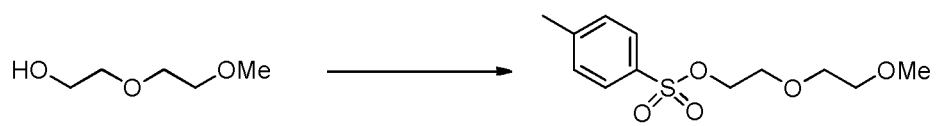
FIG. 2 is a synthetic scheme for the preparation of 2-(2-methoxyethoxy)ethyl 4-tosylate.

FIG. 2 is a synthetic scheme for the preparation of 2-(2-methoxyethoxy)ethyl 4-tosylate.

2-(2-Methoxyethoxy)ethyl 4-tosylate

Sodium hydroxide (62 g, 1.55 mol) in water (350 mL) was carefully added in one portion to 2-(2-methoxyethoxy)ethanol (110 g, 912 mmol) in tetrahydrofuran (350 mL) at 0° C. under vigorous stirring and stirred for 5 min. Then tosyl chloride (209 g, 1.09 mol) in tetrahydrofuran (350 mL) was added over 10 minutes, warmed to room temperature and stirred for 4 hours. The reaction mixture was diluted with water (350 mL) and extracted with methyl tert-butyl ether (2×700 mL). The combined organic layers were washed with 1M aqueous sodium hydroxide (2×500 mL), water (3×500 mL), dried over sodium sulfonate and concentrated to afford the title compound (221 g, 88%) as a clear oil. $^1$H NMR (500 MHz, (CD$_3$)$_2$CO) δ: 7.81 (d, J=8.0 Hz, 2H), 7.49 (d, J=8.0 Hz, 2H), 4.14-4.19 (m, 2H), 3.63-3.68 (m, 2H), 3.49-3.53 (m, 2H), 3.39-3.44 (m, 2H), 3.26 (s, 3H), 3.47 (s, 3H).

Example 3

Figure 3:
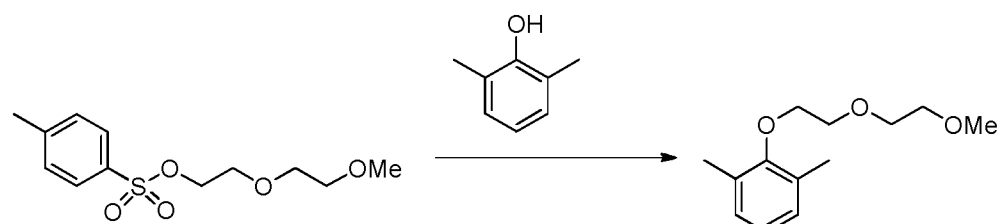
FIG. 3 is a synthetic scheme for the preparation of 2-(2-(2-methoxyethoxy)ethoxy)-1,3-dimethylbenzene.

FIG. 3 is a synthetic scheme for the preparation of 2-(2-(2-methoxyethoxy)ethoxy)-1,3-dimethylbenzene.

2-(2-(2-Methoxyethoxy)ethoxy)-1,3-dimethylbenzene

Dimethylformamide (200 mL) was added to sodium hydride (18 g as 60 weight percent in oil, 450 mmol) under nitrogen. Next, 2,6-dimethylphenol (50 g, 409 mmol) in dimethylformamide (100 mL) was added drop-wise and heated to 50° C. where 2-(2-methoxyethoxy)ethyl 4-tosylate (113 g, 413 mmol) in dimethylformamide (200 mL) was added drop-wise and stirred overnight. The reaction mixture was diluted with methyl tert-butyl ether (1 L) and washed with water (1 L). The water layer was back extracted with methyl tert-butyl ether (500 mL) and the combined organics washed with 1M potassium hydroxide (3×300 mL), hydrochloric acid (1 weight percent, 2×500 mL), water (2×500 mL), brine (1×250 mL), dried over sodium sulfate and concentrated to afford the title compound (90.5 g, 90%) as a clear oil. $^1$H NMR (300 MHz, (CD$_3$)$_2$CO) δ: 6.99 (d, J=7.8 Hz, 2H), 6.88 (t, J=7.8 Hz, 1H), 3.90-3.94 (m, 2H), 3.75-3.80 (m, 2H), 3.64-3.68 (m, 2H), 3.50-3.54 (m, 2H), 3.31 (s, 3H), 2.26 (s, 6H).

Example 4

Figure 4:
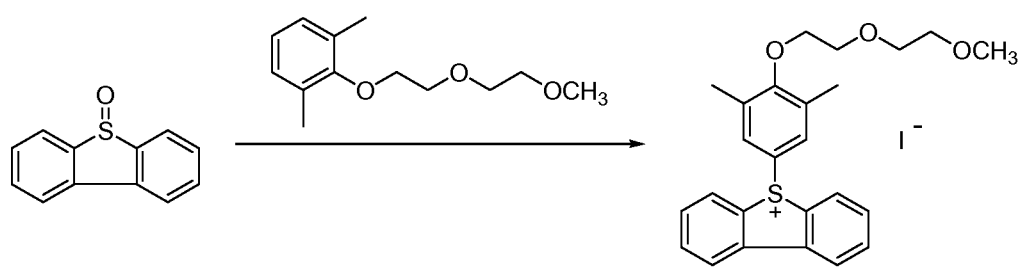
FIG. 4 is a synthetic scheme for the preparation of 5-(4-(2-(2-methoxyethoxy)ethoxy)-3,5-dimethylphenyl)-dibenzothiophen-5-ium iodide.

FIG. 4 is a synthetic scheme for the preparation of 5-(4-(2-(2-methoxyethoxy)ethoxy)-3,5-dimethylphenyl)-dibenzothiophen-5-ium iodide.

5-(4-(2-(2-Methoxyethoxy)ethoxy)-3,5-dimethylphenyl)-dibenzothiophen-5-ium iodide Eaton's Reagent (60 mL) was added to a solution of dibenzothiophene oxide (20.0 g, 0.1 mol) and 2-(2-(2-methoxyethoxy)ethoxy)-1,3-dimethylbenzene (24.7 g, 0.11 mol) in dichloromethane (60 mL) at 0° C., warmed to room temperature and stirred overnight. The reaction mixture was cooled to 0° C. and slowly quenched by the addition of water (300 mL) and washed with methyl tert-butyl ether (2×250 mL). The organic layer is discarded and sodium iodide (30 g, 0.200 mmol) in water (100 mL) was added to the aqueous layer under vigorous stirring. The precipitate was filtered and washed with copious amounts of water, suspended in minimal acetone, stirred at room temperature for 1 hour and filtered to afford the title compound (30.2 g, 57%) as an off-white solid. $^1$H NMR (500 MHz, (CD$_3$)$_2$SO) δ: 8.52 (d, J=8.0 Hz, 2H), 8.33 (d, J=8.0 Hz, 2H), 7.96 (t, J=7.5 Hz, 2H), 7.75 (d, J=7.5 Hz, 2H), 7.31 (s, 2H), 3.94 (vis t, J=5.5

Hz, 2H), 3.67 (vis t, J=5.0 Hz, 2H), 3.55 (vis t, 6.0 Hz, 2H), 3.42 (vis t, J=4.5 Hz, 2H), 3.21 (s, 3H), 2.20 (s, 6H).

Example 5

Figure 5:
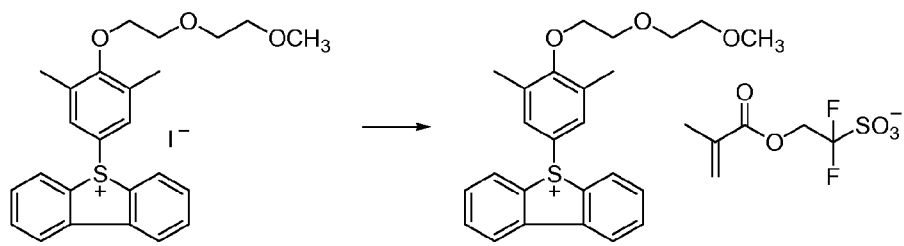
FIG. 5 is a synthetic scheme for the preparation of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate.

FIG. 5 is a synthetic scheme for the preparation of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate.

5-(4-(2-(2-Methoxyethoxy)ethoxy)-3,5-dimethylphenyl)-5H-dibenzo[b,d]thiophen-5-ium 1,1-difluoro-2-(methacryloyloxy)ethanesulfonate 5-(4-(2-(2-methoxyethoxy)ethoxy)-3,5-dimethylphenyl)-dibenzothiophen-5-ium iodide (13.0 g, 24.3 mmol) and triethylammonium 1,1-difluoro-2-(methacryloyloxy)ethanesulfonate (8.22 g, 24.8 mmol) were dissolved in dichloromethane (150 mL) and water (150 mL) and stirred at room temperature overnight. The layers were separated and the organic layer was washed with water (8×150 mL) and concentrated under reduced pressure to afford the title compound (15.1 g, 97%) as a white hydroscopic solid which was stored under inert nitrogen atmosphere. $^1$H NMR (500 MHz, (CD$_3$)$_2$CO) δ: 8.52 (d, J=8.0 Hz, 2H), 8.38 (d, J=8.5 Hz, 2H), 8.00 (t, J=7.5 Hz, 2H), 7.80 (t, J=8.0 Hz, 2H), 7.51 (s, 2H), 6.13-6.16 (m, 1H), 5.67-5.69 (m, 1H), 4.77 t, J=15.5 Hz, 2H), 4.02-4.05 (m, 2H0, 3.73-3.77 (m, 2H), 3.58-3.62 (m, 2H), 3.44-3.49 (m, 2H), 3.25 (s, 3H), 2.26 (s, 6H), 1.13 (s, 3H).

Example 6

Figure 6:
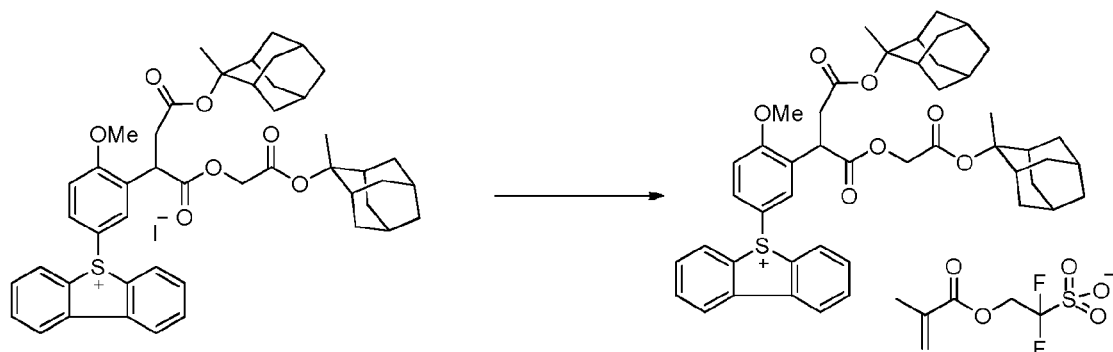
FIG. 6 is a synthetic scheme for the preparation of 5-(4-methoxy-3-(4-(((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate.

FIG. 6 is a synthetic scheme for the preparation of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate.

5-(4-Methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (37.8 g, 47.4 mmol and N,N,N-trimethyl-1-phenylmethanaminium 1,1-difluoro-2-(methacryloyloxy)ethanesulfonate (18.9 g, 49.8 mmol) were dissolved in DCM (250 mL) and water (250 mL) and stirred at 25° C. overnight. The layers were separated, the aqueous phase extracted with dichloromethane (100 mL), the combined organic layers washed with water (8×200 mL) and concentrated under reduced pressure to afford the title compound (36.0, 77%) as an off white solid. $^1$H NMR (500 MHz, (CD$_3$)$_2$CO) δ: (8.52-8.56 (m, 2H), 8.37 (d, J=8 Hz, 1H), 8.31 (d, J=8.5 Hz, 1H), 7.99-8.06 (m, 2H), 7.78-7.85 (m, 3H), 7.63 (dd, J=9, 1.5 Hz, 1H), 7.31 (d, J=9 Hz, 1H), 6.16-6.19 (m, 1H), 5.64-6.69 (m, 1H), 5.62 (s, 2 h), 4.72-4.79 (m, 2H), 4.50-4.65 (m, 2H), 4.42-4.47 (m, 1H), 3.96 (s, 3H), 2.99-3.07 (m, 1H), 2.63-2.70 (m, 1H), 2.10-2.30 (m, 4H), (1.42-2.09 (m, 31H).

Example 7

Figure 7:
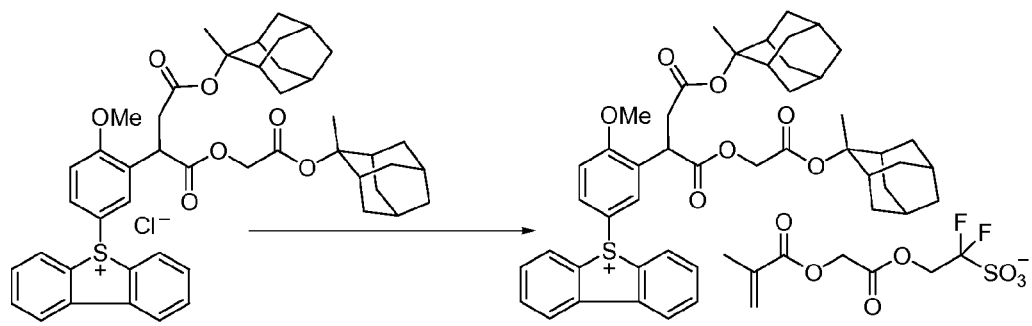
FIG. 7 is a synthetic scheme for the preparation of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

FIG. 7 is a synthetic scheme for the preparation of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

5-(4-Methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl) phenyl)-5H-dibenzo[b,d]thiophen-5-ium 1,1-difluoro-2-(2-(methacryloyloxy)acetoxy) ethanesulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium chloride (40.0 g, 50.2 mmol) and N,N,N-trimethyl-1-phenylmethanaminium 1,1-difluoro-2-(2-(methacryloyloxy)acetoxy)ethanesulfonate (23.0 g, 52.6 mmol) were dissolved in dichloromethane (300 mL) and water (300 mL) and stirred at room temperature overnight. The layers were separated, the organic phase washed with water (7×250 mL) and concentrated to afford the title compound (43.4 g, 83%) as a white solid. $^1$H NMR (300 MHz, (CD$_3$)$_2$SO) δ: 8.52 (d, J=7.8 Hz, 2H), 8.31 (d, J=8.1 Hz, 1H), 8.26 (d, J=8.1 Hz, 1H), 7.97 (t, J=7.8 Hz, 2H), 7.75 (t, J=7.8 Hz, 2H), 7.71 (d, J=2.4 Hz, 1H), 7.35 (dd, J=9.0, 2.4 Hz, 1H), 7.22 (d, J=9.0 Hz, 1H), 6.12-6.17 (m, 1H), 5.76-5.82 (m, 1H), 4.87 (s, 2H), 4.63 (t, J=15.6 Hz, 2H), 4.59 (s, 2H), 4.35 (t, J=7.5 Hz, 1H), 3.82 (s, 3H), 2.92-3.10 (m, 2H), 2.56-2.68 (m, 1H), 1.35-2.25 (m, 36H).

Example 8

Figure 8:
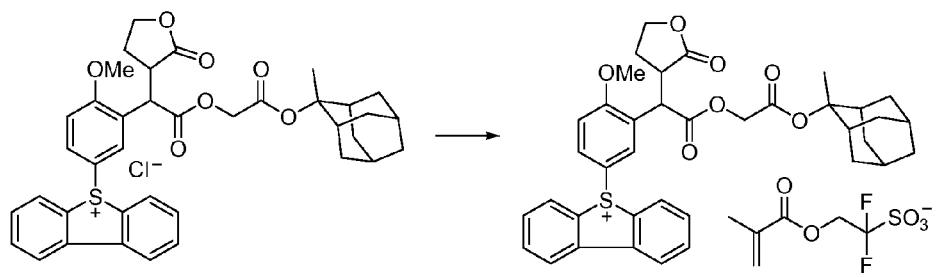
FIG. 8 is a synthetic scheme for the preparation of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

FIG. 8 is a synthetic scheme for the preparation of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

5-(4-Methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d] thiophen-5-ium 1,1-difluoro-2-(methacryloyloxy) ethanesulfonate 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium chloride (40.0 g, 59.2 mmol) and N,N,N-trimethyl-1-phenylmethanaminium 1,1-difluoro-2-(methacryloyloxy)ethanesulfonate (23.6 g, 62.2 mmol) were dissolved in dichloromethane (300 mL) and water (300 mL) and stirred at room temperature overnight. The layers were separated, the organic phase washed with water (7×250 mL), concentrated to half volume and precipitated into methyl tert-butyl ether (1.5 L). The precipitate was filtered, washed with methyl tert-butyl ether (2×500 mL) and dried to afford the title compound (39.1 g, 76%) as a white solid. $^1$H NMR (300 MHz, (CD$_3$)$_2$SO) δ: 8.53 (d, J=7.8 Hz, 2H), 8.34 (d, J=8.1 Hz, 2H), 8.27 (d, J=7.8 Hz, 2H), 7.97 (t, J=7.5 Hz, 2H), 7.75 (dt, J=7.8, 2.7 Hz, 1H), 7.68 (d, J=1.8 Hz, 1H), 7.38 (dd, J=9.0, 2.1 Hz, 1H), 7.23 (d, J=9.0 Hz, 1H), 6.12 (vis s, 1H), 5.77 (vis s, 1H), 4.64 (t, J=15.6 Hz, 2H), 4.60 (s, 2H), 4.25 (d, J=7.2 Hz, 1H), 4.05-4.21 (m, 2H), 3.82 (s, 3H), 3.36-3.51 (m, 2H), 2.14-2.20 (m, 1H), 1.38-2.04 (m, 17H).

Example 9

In general polymer molecular weight were determined from $^{13}$C NMR spectra obtained on a Varian 300 Megahertz NMR spectrometer operating with a relaxation delay of 2 seconds by integration of initiator end groups and one of the carbons of the PAG unit.

Figure 9:
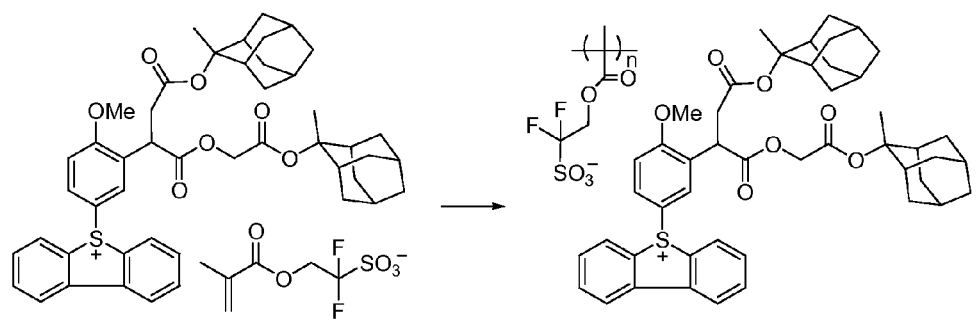
FIG. 9 is a synthetic scheme for the preparation of a homopolymer of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate.

FIG. 9 is a synthetic scheme for the preparation of a homopolymer of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate.

Homopolymer of 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate 5-(4-methoxy-3-(4-((2-methyladamantan-2-yl)oxy)-1-(2-((2-methyladamantan-2-yl)oxy)-2-oxoethoxy)-1,4-dioxobutan-2-yl)phenyl)-dibenzothiophenium 1,1-difluoro-2-(methacryloyloxy)ethanesulfonate (10.0 g, 10.2 mmol) was dissolved in ethyl lactate/gamma-butyrolactone (3/7 v/v, 15.0 g). The initiator 2,2'-azobis(2,4-dimethyl valeronitrile) (1.00 g) was dissolved in acetonitrile/tetrahydrofuran (2/1 v/v, 1.00 g). The monomer and initiator solutions were added drop-wise over 4 hours to a flask preheated to 80° C. followed by an initiator chase. The reaction mixture was stirred for 2 hours, cooled to room temperature, diluted with methanol (17 g) and precipitated into diisopropyl ether (800 g). The polymer was filtered and dried to afford the title compound (8.00 g, 80%, weight average molecular weight 3972) as a white solid.

Example 10

Figure 10:
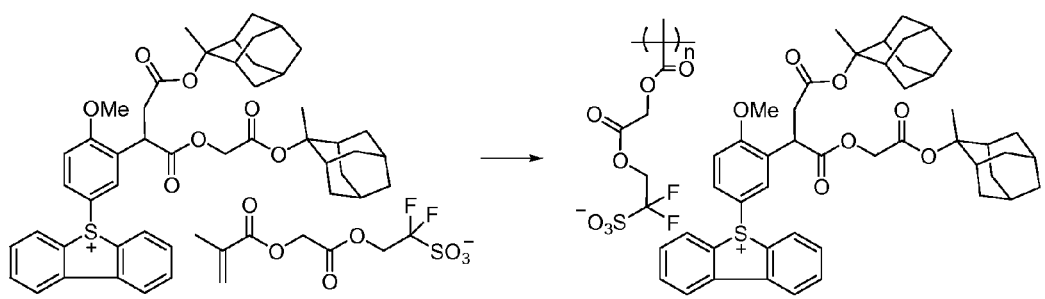
FIG. 10 is a synthetic scheme for the preparation of a homopolymer of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

FIG. 10 is a synthetic scheme for the preparation of a homopolymer of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

Homopolymer of 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate (1.00 g, 0.953 mmol) was dissolved in ethyl lactate/gamma-butyrolactone (3/7 v/v, 1.50 g). 2,2'-Azobis(2.4-dimethyl valeronitrile) (0.150 g) was dissolved in acetonitrile/tetrahydrofuran (2/1 v/v, 0.150 g). The monomer and initiator solutions were added drop-wise to a flask preheated to 75° C. and stirred for 8 h. The reaction mixture was cooled to room temperature, diluted with acetone (0.900 g) and precipitated as a sticky solid from acetone/diisopropylether (1:1 25.0 g), decanted, redissolved in acetone (2.40 g) and methanol (0.500 g) and precipitated into diisopropyl ether (20× reaction volume). The polymer was filtered and dried to afford the title compound (0.550 g, 55%, weight average molecular weight 3,000 daltons) as a white solid.

Example 11

Figure 11:
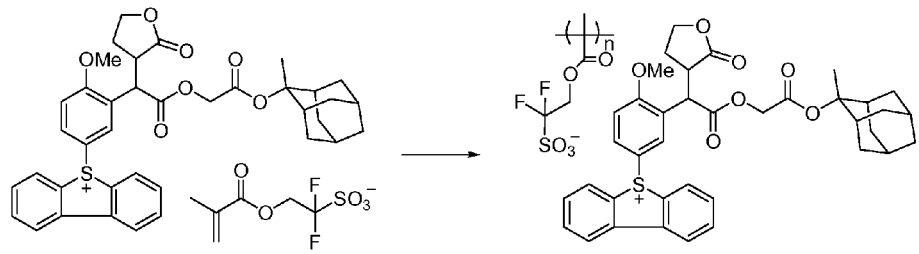
FIG. 11 is a synthetic scheme for the preparation of a homopolymer of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

FIG. 11 is a synthetic scheme for the preparation of a homopolymer of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

Homopolymer of 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate (15.0 g, 17.3 mmol) was dissolved in ethyl lactate/gamma-butyrolactone (3/7 v/v, 60.0 g). 2,2'-Azobis(2.4-dimethyl valeronitrile) (2.25 g) was dissolved in acetonitrile/tetrahydrofuran (2/1 v/v, 2.25 g). The monomer and initiator solutions were added drop-wise over 4 hours to a flask preheated to 90° C. The reaction mixture was cooled to room temperature, diluted with tetrahydrofuran (10× reaction volume) and acetone (5× reaction volume) and precipitated into diisopropyl ether (2000 g). The polymer was filtered and dried to afford the title compound (7.96 g, 53%, weight average molecular weight 3,476 daltons) as a white solid.

Example 12

Figure 12:
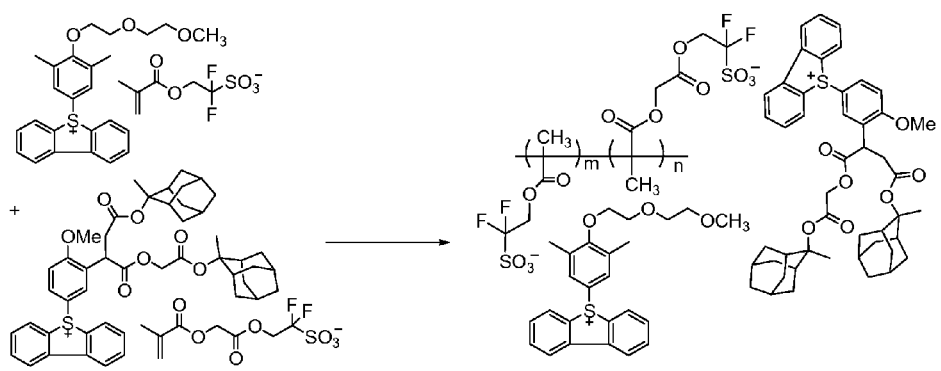
FIG. 12 is a synthetic scheme for the preparation of a copolymer of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

FIG. 12 is a synthetic scheme for the preparation of a copolymer of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate.

Copolymer of 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate (3.00 g, 8.25 mmol) and 5-(4-methoxy-3-(4-(((1R,3S,5r,7r)-2-methyladamantan-2-yl)oxy)-1-(2-(((1R,3S,5r,7r)-2-methyladamantan-2-yl)oxy)-2-oxoethoxy)-1,4-dioxobutan-2-yl)phenyl)-5H-dibenzo[b,d]thiophen-5-ium 1,1-difluoro-2-(2-(methacryloyloxy)acetoxy)ethanesulfonate (7.00 g, 6.67 mmol) were dissolved in ethyl lactate/gamma-butyrolactone (3/7 v/v, 15.0 g). 2,2'-Azobis(2.4-dimethyl valeronitrile) (1.50 g) was dissolved in acetonitrile/tetrahydrofuran (2/1 v/v, 1.50 g). The monomer and initiator solutions were added drop-wise to a flask preheated to 75° C. over 4 hours. The reaction mixture was cooled to room temperature, precipitated as a sticky solid from methanol/diisopropyl ether (1:1, 20× reaction volume), redissolved into acetone (20.0 mL) and methanol (0.300 g) and reprecipitated from diisopropyl ether/methanol (19:1 v/v, 2,000 mL), filtered and dried to afford the title compound (6.00 g, 60%, weight average molecular weight 2,500) as a white solid.

Example 13

Figure 13:
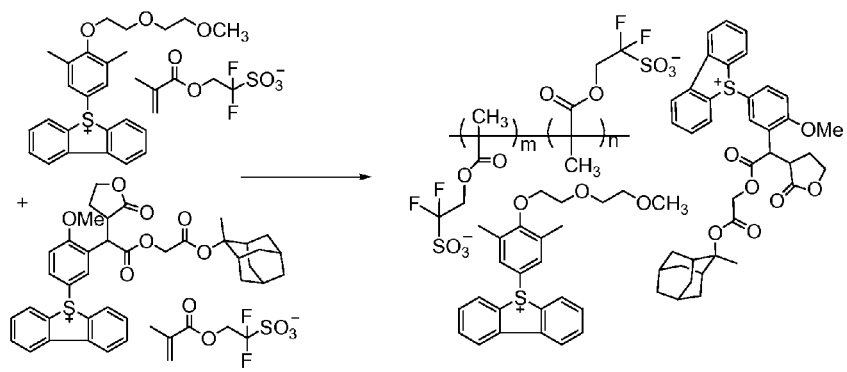
FIG. 13 is a synthetic scheme for the preparation of a copolymer 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

FIG. 13 is a synthetic scheme for the preparation of a copolymer 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate.

Copolymer 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate and 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate 5-(4-(2-(2-methoxyethoxy)ethoxy)-3,5-dimethylphenyl)-5H-dibenzo[b,d]thiophen-5-ium 1,1-difluoro-2-(methacryloyloxy)ethanesulfonate (4.50 g, 12.4 mmol) and 5-(4-methoxy-3-(2-(2-(((1R,3S,5r,7r)-2-methyladamantan-2-yl)oxy)-2-oxoethoxy)-2-oxo-1-(2-oxotetrahydrofuran-3-yl)ethyl)phenyl)-5H-dibenzo[b,d]thiophen-5-ium 1,1-difluoro-2-(methacryloyloxy)ethanesulfonate (10.5 g, 12.1 mmol) were dissolved in ethyl lactate/gamma-butyrolactone (3/7 v/v, 60.0 g). 2,2'-Azobis(2.4-dimethyl valeronitrile) (2.25 g) was dissolved in acetonitrile/tetrahydrofuran (2/1 v/v, 2.25 g). The monomer and initiator solutions were added dropwise to a flask preheated to 75° C. over 4 h. The reaction mixture was cooled to room temperature, diluted with tetrahydrofuran (5× reaction volume) and acetone (5× reaction volume), precipitated from diisopropyl ether (20× reaction volume), filtered and dried to afford the title compound (11.0 g, 73%, weight average molecular weight 2,700 daltons) as a white solid.

Example 14

Preparation of Tetrapolymer with Acid Generator Units

A heel solution was made by dissolving 2-phenylpropan-2-yl methacrylate (0.39 g), 2-oxotetrahydrofuran-3-yl methacrylate (0.33 g), 3,5-bis(1,1,1,3,3,3-hexafluoro-2-hydroxypropan-2-yl)cyclohexyl methacrylate (0.57 g) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate (0.31 g) in 12.81 g ethyl lactate/gamma-butyrolactone (7/3 v/v). Feed solution was prepared by dissolving 2-phenylpropan-2-yl methacrylate (185.54 g, 0.967 mol), 2-oxotetrahydrofuran-3-yl methacrylate (204.27 g, 1.26 mol), 3,5-bis(1,1,1,3,3,3-hexafluoro-2-hydroxypropan-2-yl)cyclohexyl methacrylate (127.98 g, 0.29 mol) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate (81.5 g, 0.132 mol) in 606 g ethyl lactate: gamma-butyrolactone (30/70 v/v). Initiator solution was prepared by dissolving 65.96 g initiator (2,2'-azobis(2,4-dimethyl valeronitrile)) in 66 g acetonitrile/tetrahydrofuran (2/1 v/v). The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then stirred for additional 2 hours, whereby, the reaction was quenched using hydroquinone (2.0 g). The contents were cooled to room temperature and precipitated twice out of 10× (by weight) diisopropyl ether/methanol 95/5 (w/w). The polymer obtained was dried under vacuum after each precipitation step at 50° C. for 24 hours to yield 500 g polymer having a weight average molecular weight of 5,200 daltons, a dispersity of 1.5, and a monomer composition of the respective monomers of 36.0 mole percent, 47.5 mole percent, 11.0 mole percent, and 5.5 mole percent.

Example 15

Preparation of Tetrapolymer with Acid Generator Units

The process of Example 14 was repeated, except that equimolar 5-phenyl-5H-dibenzo[b,d]thiophenium 1,1-difluoro-2-(methacryloyloxy)ethanesulfonate was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate. The polymer obtained had a weight average molecular weight of 6,300 daltons, a dispersity of 1.4, and respective monomer contents of 36.5 mole percent, 47.5 mole percent, 12.0 mole percent, and 5 mole percent.

Example 16

Preparation of Tetrapolymer with Acid Generator Units (TBPPDBTS-F2)

The process of Example 14 was repeated, except that equimolar 5-(4-(tert-butyl)phenyl)-5H-dibenzo[b,d]thiophen-5-ium 1,1-difluoro-2-(methacryloyloxy)ethanesulfonate was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate. The polymer obtained had a weight average molecular weight of 5,200 daltons, a dispersity of 1.6, and respective monomer contents of 34 mole percent, 51 mole percent, 9 mole percent, and 6 mole percent.

Example 17

Preparation of Tetrapolymer with Acid Generator Units

The process of Example 14 was repeated, except that an equimolar amount of the monomer of Example 9 was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate. The polymer obtained had a weight average molecular weight of 5,200 daltons, a dispersity of 1.5, and respective monomer contents of 38 mole percent, 46 mole percent, 10 mole percent, and 6 mole percent.

Example 18

Preparation of Terpolymer without Acid Generator Units

Heel solution was made by dissolving 2-phenylpropan-2-yl methacrylate (1.94 g), 2-oxotetrahydrofuran-3-yl methacrylate (1.7 g), 3,5-bis(1,1,1,3,3,3-hexafluoro-2-hydroxypropan-2-yl)cyclohexyl methacrylate (2.81 g) in 72 g ethyl lactate: gamma-butyrolactone (30/70 v/v). Feed solution was prepared by dissolving 2-phenylpropan-2-yl methacrylate (33.08 g), 2-oxotetrahydrofuran-3-yl methacrylate (35.97 g), 3,5-bis(1,1,1,3,3,3-hexafluoro-2-hydroxypropan-2-yl)cyclohexyl methacrylate (23.91 g) in 94 g ethyl lactate: gamma-butyrolactone (30/70 v/v). Initiator solution was prepared by dissolving 11 g initiator (2,2'-azobis(2,4-dimethyl valeronitrile)) in 11 g acetonitrile/tetrahydrofuran (2/1 v/v). The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pumps over a 4 hour time period. The contents were then stirred for additional 2 hours, after which the reaction was quenched using hydroquinone (1.0 g). The contents were cooled to room temperature and precipitated twice out of 10× (by weight) isopropyl ether/methanol 95/5 (w/w). The polymer obtained was dried under vacuum after each precipitation step at 50° C. for 24 hours to yield 100 g polymer having a weight average molecular weight of 5,000 daltons, a dispersity of 1.5, and respective monomer contents of 43 mole percent, 46 mole percent, and 11 mole percent.

Example 19

Preparation and Processing of a Photoresist Composition

Non-polymeric photoacid generators and photo-destroyable quenchers (collectively, "additives") used in the preparation of photoresist compositions are summarized in Table 1. Photoresist compositions are summarized in Table 2. The Example 19 positive-tone photoresist composition was prepared by combining component 1, 5.33 g of a 10 weight percent solution of the polymer of Example 17 in ethyl lactate; component 2, 10.373 g of a 2 weight percent solution of the additive A-1 in ethyl lactate; component 3, 0.320 g of a 0.5 weight percent solution of tetrakis(2-hydroxypropyl) ethylenediamine in ethyl lactate; component 4, 0.356 g of a 2 weight percent solution of the additive A-2 in ethyl lactate; component 5, 0.107 g of a 0.5 weight percent solution of fluorinated surfactant (Omnova PF656) in ethyl lactate; component 6, 4.737 g of ethyl lactate; and component 7, 8.775 g of 2-hydroxyisobutyric acid methyl ester. The formulated resist was passed through a 0.01 micrometer (μm) polytetrafluoroethylene (PTFE) filter. The thus prepared resist was spin coated onto a silicon wafer, soft baked to remove carrier solvent and exposed through a photomask to EUV radiation. The imaged resist layer was then baked at 110° C. for 60 seconds and then developed with an aqueous alkaline composition.

TABLE 1

| Additive | Structure |
| --- | --- |
| A-1 | 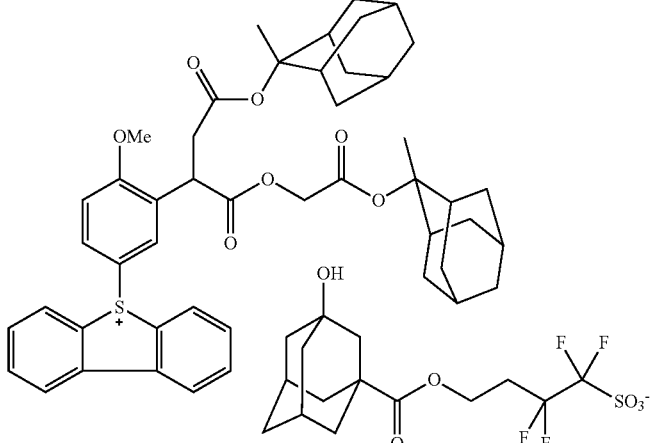 |
| A-2 | 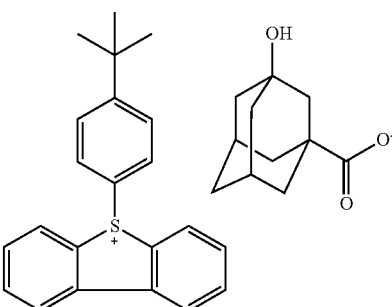 |

TABLE 1-continued
| Additive | Structure |
| --- | --- |
| A-3 | 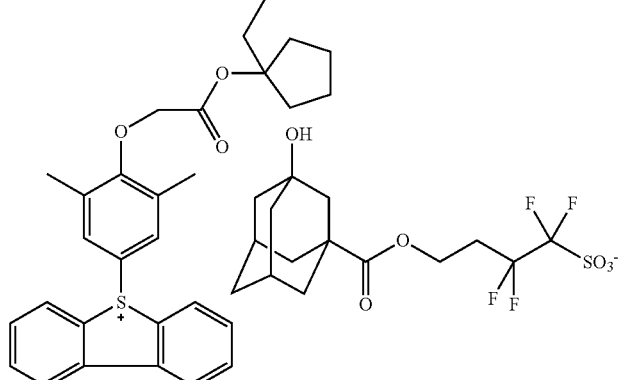 |
| A-4 | 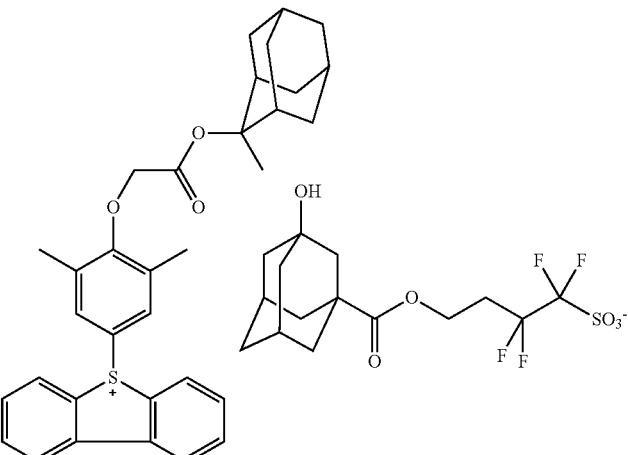 |
| A-5 | 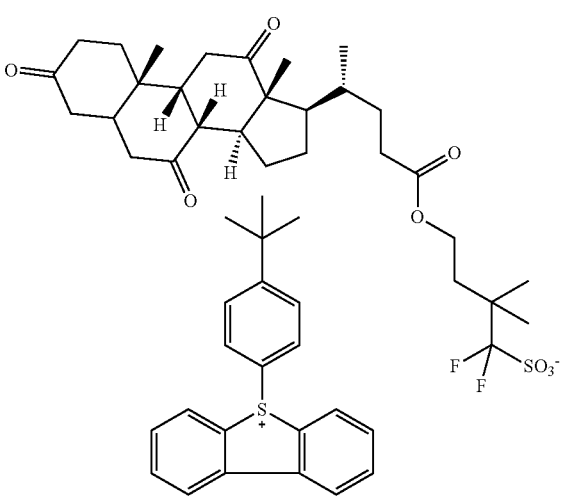 |

TABLE 1-continued

| Additive | Structure |
|---|---|
| A-6 | 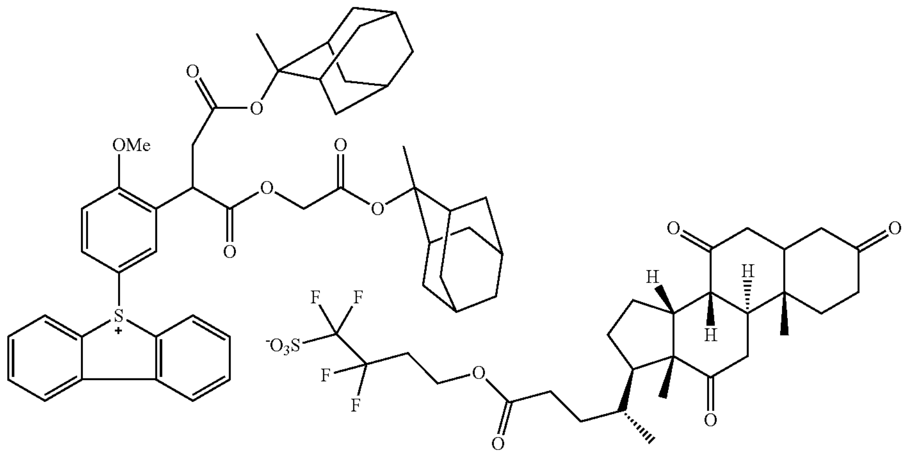 |
| A-7 | 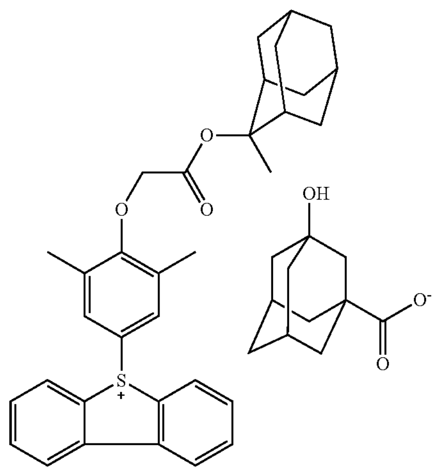 [SMILES: Cc1cc(-[s+]2c3ccccc3c3ccccc32)cc(C)c1OCC(=O)OC1(C)C2CC3CC(C2)CC1C3 ; O=C([O-])C12CC3CC(CC(O)(C3)C1)C2] |

For Table 2, below, components 1-7 correspond to the descriptions in Example 19. Component amounts, in brackets, are expressed in units of grams.

TABLE 2

| Ex. | Comp. 1 polymer | Comp. 2 PAG/polyPAG | Comp. 3 quencher | Comp. 4 PDQ | Comp. 5 surfactant | Comp. 6 solvent | Comp. 7 solvent |
|---|---|---|---|---|---|---|---|
| 19 (C) | Ex. 17 [5.330] | A-1 [10.37] | [0.320] | A-2 [0.356] | [0.107] | [4.737] | [8.775] |
| 20 (C) | Ex. 16 [9.378] | A-1 [14.79] | [0.563] | A-2 [0.626] | [0.188] | [9.826] | [14.63] |
| 21 (C) | Ex. 15 [15.92] | — | [0.478] | — | [0.318] | [25.76] | [17.52] |
| 22 (C) | Ex. 14 [55.4] | A-3 [94.24] | [13.30] | — | [1.109] | [48.17] | [87.75] |
| 23 (C) | Ex. 18 [6.292] | A-4 [8.148] | [1.443] | — | [0.126] | [12.23] | [11.76] |
| 24 (C) | Ex. 18 [7.283] | A-5 [13.31] | [0.954]* | — | [0.146] | [13.61] | [14.70] |
| 25 (C) | Ex. 18 [6.458] | A-6 [17.47] | [0.846]* | — | [0.129] | [10.40] | [14.70] |
| 26 (I) | Ex. 14 [8.850] | Ex. 9 [17.64] | [2.120] | — | [0.177] | [6.570] | [14.63] |
| 27 (I) | Ex. 14 [5.272] | Ex. 9 [10.507] | [0.618] | A-7 [0.451] | [0.105] | [4.271] | [8.775] |
| 28 (I) | Ex. 16 [5.700] | Ex. 9 [11.14] | [1.308] | — | [0.114] | [9.974] | [11.76] |

TABLE 2-continued

| Ex. | Comp. 1 polymer | Comp. 2 PAG/polyPAG | Comp. 3 quencher | Comp. 4 PDQ | Comp. 5 surfactant | Comp. 6 solvent | Comp. 7 solvent |
|---|---|---|---|---|---|---|---|
| 29 (I) | Ex. 18 [5.700] | Ex. 9 [11.14] | [1.308] | — | [0.114] | [9.974] | [11.76] |
| 30 (C) | Ex. 16 [7.980] | — | [0.239] | — | [0.160] | [19.861] | [11.76] |

*Triisopropanolamine

Critical Dimension Uniformity.

Critical dimension uniformity (CDU) is the calculated 3 Sigma (three standard deviations) for ten Fields of View (FOV) measuring 36 contact holes for each FOV, all taken at Best Exposure/Best Focus. Each data point has been pre-normalized to a standard EUV photoresist which is run in each lithographic slot to eliminate variability and noise. The results, presented in Tables 3 and 4, show that the lowest (best) CDU values are exhibited by the inventive Examples 26 and 27 photoresists with polymer comprising 50 to 100 mole percent of photoacid-generating repeat units. These inventive examples outperformed comparative examples with polymers having less than 50 mole percent of photoacid-generating repeat units, with or without non-polymer-bound photoacid generator. In Tables 3 and 4, the CDU of Examples 26 and 27 are normalized to 1, and designated with " ◇ ". Comparative examples which underperform relative to the example by 0-15% are designated with"●"; comparative examples which underperform relative to the example by 15-35% are designated with "■"; and comparative examples which underperform relative to the example by >35% are designated with "□". In Table 3, "PolyPAG" refers to a polymer comprising 50 to 100 mole percent of photoacid-generating repeat units, "Polymer-bound-PAG" refers to a polymer comprising photoacid-generating repeat units in an amount less than 50 mole percent, and "free PAG" refers to a non-polymer-bound photoacid-generator.

TABLE 3

| Example | PAG Type | CDU Normalized |
|---|---|---|
| Example 26 | PolyPAG + Polymer-bound-PAG | ◇ |
| Comparative Example 19 | Polymer-bound-PAG + free PAG | ■ |
| Comparative Example 20 | Polymer-bound-PAG + free PAG | □ |
| Comparative Example 21 | Polymer-bound-PAG | □ |
| Comparative Example 22 | Polymer-bound-PAG + free PAG | ■ |

TABLE 4

| Example | PAG Type | CDU Normalized |
|---|---|---|
| Example 27 | PolyPAG + Polymer-bound-PAG | ◇ |
| Comparative Example 19 | Polymer-bound-PAG + free PAG | ● |
| Comparative Example 20 | Polymer-bound-PAG + free PAG | ■ |
| Comparative Example 21 | Polymer-bound-PAG | ■ |
| Comparative Example 22 | Polymer-bound-PAG + free PAG | ● |

Contact Hole Exposure Latitude.

Exposure latitude % (EL %) were calculated from critical dimension (CD) data through dose and focus (FEM) with 10% CD boundaries restricted to 100 nm depth of focus (DoF) for 30 nm contact holes at 1:1 half pitch. The results, presented in Table 5, show that the largest (best) exposure latitude is exhibited by the inventive Example 26, which contains a polymer comprising 50 to 100 mole percent of photoacid-generating repeat units in combination with a polymer having less than 50 mole percent of photoacid-generating repeat units. This inventive example outperformed comparative examples with polymers having less than 50 mole percent of photoacid-generating repeat units and non-polymer-bound photoacid generator. In Table 5, the exposure latitude of Examples 26 is normalized to 1, and designated with " ◇ ". Comparative examples which underperform relative to the example by 0-10% are designated with"●"; comparative examples which underperform relative to the example by 10-20% are designated with "■"; and comparative examples which underperform relative to the example by >20% are designated with "□".

TABLE 5

| Example | PAG Type | CDU Normalized |
|---|---|---|
| Example 26 | PolyPAG + Polymer-bound-PAG | ◇ |
| Comparative Example 19 | Polymer-bound-PAG + free PAG | ■ |
| Comparative Example 20 | Polymer-bound-PAG + free PAG | □ |
| Comparative Example 22 | Polymer-bound-PAG + free PAG | ■ |

Line Width Roughness.

LWR values were determined by top-down scanning electron microscopy (SEM) using a Hitachi 9380 CD-SEM, operating at an accelerating voltage of 800 volts (V), probe current of 8.0 picoamperes (pA), using 200 Kx magnification at 1.0 digital zoom, with the number of frames set to 64. LWR was measured over a 2 μm line length in steps of 40 nm, and reported as the average LWR for the measured region. The results, presented in Table 6, shows that the lowest (best) LWR values are exhibited by the inventive Examples 28 and 29. In Table 6, the LWR of Examples 28 and 29 show significant improvement over the comparative examples Improved LWR by 20-40% is designated with "■"; and improved LWR>40% is designated with "□". The inventive Example 28 photoresist contains photoacid generator in the form of polymer comprising 50 to 100 mole percent of photoacid-generating repeat units, and polymer comprising 50 to 100 mole percent of photoacid-generating repeat units. The inventive Example 29 photoresist composition contains photoacid generator in the form of polymer comprising 50 to 100 mole percent of photoacid-generating repeat units. The Comparative Example 30 photoresist composition contains photoacid generator in the form of a polymer comprising less than 50 mole percent of photoacid-generating repeat units. The Comparative Example 23, 24, and 25 photoresist compositions contain photoacid generator in the form of free photoacid generator.

TABLE 6

| Comparative Example | LWR Improvement @ 24 nm with Example 28 | LWR Improvement @ 24 nm with Example 29 |
|---|---|---|
| 30 | □ | □ |
| 23 | ■ | ■ |
| 24 | □ | □ |
| 25 | □ | □ |

Line and Space Exposure Latitude.

Exposure latitude percent (EL %) values were calculated from critical dimension (CD) data through dose and focus (FEM) with 10% CD boundaries restricted to 100 nm depth of focus (DoF) for 25 nm lines and spaces at 1:1 half pitch. The results, presented in Table 7, shows that the largest (best) exposure latitude is exhibited by the inventive Example 28. Improved performance is marked with "◊"; similar performance is designated with "●"; and inferior performance is marked with "▶".

TABLE 7

| Example | PAG Type | EL |
|---|---|---|
| Example 28 | PolyPAG + Polymer-bound-PAG | ◊ |
| Example 29 | PolyPAG | ● |
| Comparative Example 23 | Free PAG | ▶ |
| Comparative Example 24 | Free PAG | ▶ |
| Comparative Example 25 | Free PAG | ▶ |

The invention claimed is:

1. A photoresist composition comprising:
a first polymer comprising 60 to 100 mole percent of photoacid-generating repeat units, wherein each of the photoacid-generating repeat units comprises (a) photoacid-generating functionality and (b) base-solubility-enhancing functionality selected from the group consisting of tertiary carboxylic acid esters, secondary carboxylic acid esters wherein the secondary carbon is substituted with at least one unsubstituted or substituted $C_{6-40}$ aryl, acetals, ketals, lactones, sultones, alpha-fluorinated esters, beta-fluorinated esters, alpha, beta-fluorinated esters, polyalkyleneglycols, alpha-fluorinated alcohols, and combinations thereof; and
a second polymer that exhibits a change in solubility in an alkali developer under the action of acid
wherein the photoacid-generating repeat units of the first polymer have the structure

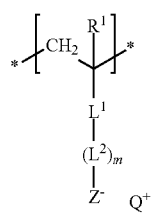

wherein
$R^1$ is independently in each of the repeat units H, F, —CN, $C_{1-10}$ alkyl, or $C_{1-10}$ fluoroalkyl;
$L^1$ is independently in each of the repeat units —O—, —C(O)—O—, unsubstituted $C_{6-18}$ arylene, or substituted $C_{6-18}$ arylene;
m is 1;
$L^2$ is independently in each of the repeat units an unsubstituted or substituted $C_{1-20}$ hydrocarbylene, wherein the substituted $C_{1-20}$ hydrocarbylene can, optionally, include one or more in-chain divalent heteroatom-containing groups that is —O—, —S—, —$NR^2$, —$PR^2$—, —C(O)—, —OC(O)O—, —N($R^2$)C(O)—, —C(O)N($R^2$)—, —OC(O)N($R^2$)—, —N($R^2$)C(O)O—, —S(O)—, —S(O)$_2$—, —N($R^2$)S(O)$_2$—, —S(O)$_2$N($R^2$)—, —OS(O)$_2$—, or —S(O)$_2$O—, wherein $R^2$ is H or $C_{1-12}$ hydrocarbyl;
$Z^-$ is independently in each of the repeat units sulfonate (—SO$_3^-$), sulfonamidate (anion of sulfonamide; —S(O)$_2$N$^-R^3$, wherein $R^3$ is H or unsubstituted or substituted $C_{1-12}$ hydrocarbyl), or sulfonimidate (anion of sulfonimide; —S(O)$_2$N$^-$S(O)$_2R^3$, wherein $R^3$ is H or unsubstituted or substituted $C_{1-12}$ hydrocarbyl);
$Q^+$ is photoacid-generating cation; and
at least one of $L^1$, $L^2$ (when m is 1), and $Q^+$ comprises the base-solubility-enhancing functionality.

2. The photoresist composition of claim 1, wherein the first polymer comprises 95 to 100 mole percent of the photoacid-generating repeat units, and wherein the photoacid-generating repeat units are derived from a single monomer.

3. The photoresist composition of claim 1, wherein the first polymer comprises 95 to 100 mole percent of the photoacid-generating repeat units, and wherein the photoacid-generating repeat units are derived from at least two different monomers.

4. The photoresist composition of claim 1, wherein
$R^1$ is independently in each of the photoacid-generating repeat units H or methyl;
$L^1$ is —C(O)—O— in each of the photoacid-generating repeat units;
m is 1 in each of the photoacid-generating repeat units;
$L^2$ is independently in each of the photoacid-generating repeat units a fluorine-substituted $C_{2-20}$ hydrocarbylene, wherein the fluorine-substituted $C_{2-20}$ hydrocarbylene can, optionally, include one or more in-chain divalent heteroatom-containing groups that is —O—, —OC(O)—, or —C(O)O—;
$Z^-$ is sulfonate (—SO$_3^-$) in each of the photoacid-generating repeat units; and
$Q^+$ is independently in each of the photoacid-generating repeat units an unsubstituted or substituted tri($C_{1-40}$-hydrocarbyl)sulfonium ion, or an unsubstituted or substituted di($C_{1-40}$-hydrocarbyl)iodonium ion.

5. The photoresist composition of claim 4,
wherein the second polymer comprises 10 to 65 mole percent of acid-labile repeat units, 0 to 50 weight percent of base-labile repeat units, 0 to 40 mole percent of base-soluble repeat units, and 0 to 15 mole percent of photoacid-generating repeat units;
wherein the photoresist composition comprises, on a dry weight basis,
20 to 80 weight percent of the first polymer,
10 to 60 weight percent of the second polymer, and
0.5 to 10 weight percent of a quencher.

6. A method of forming an electronic device, comprising:
(a) applying a layer of the photoresist composition of claim 1 on a substrate;

(b) pattern-wise exposing the photoresist composition layer to activating radiation; and
(c) developing the exposed photoresist composition layer to provide a resist relief image.

* * * * *